US 6,564,107 B1

(12) United States Patent
Bodner et al.

(10) Patent No.: US 6,564,107 B1
(45) Date of Patent: May 13, 2003

(54) COIL-LESS LEAD SYSTEM

(75) Inventors: Jeff Bodner, Roseville, MN (US); Mohan Krishnan, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 342 days.

(21) Appl. No.: 09/642,802

(22) Filed: Aug. 21, 2000

(51) Int. Cl.[7] .................................................. A61N 1/00
(52) U.S. Cl. ........................................ 607/122; 427/2.1
(58) Field of Search ............................... 606/41, 46–50; 604/22; 427/2.24–2.25, 2.28, 2.12, 2.1, 2.3; 607/122–132; 174/98

(56) References Cited

U.S. PATENT DOCUMENTS

| | | | | |
|---|---|---|---|---|
| 2,888,928 A | * | 6/1959 | Seiger ........................... 606/49 |
| 3,781,982 A | * | 1/1974 | Ziemek et al. ............ 174/125.1 |
| 3,828,780 A | * | 8/1974 | Morrison, Jr. ............... 604/119 |
| 3,906,955 A | * | 9/1975 | Roberts ......................... 604/21 |
| 4,006,047 A | | 2/1977 | Brummett et al. ........... 156/656 |
| 4,269,174 A | * | 5/1981 | Adair ........................... 128/842 |
| 4,311,143 A | * | 1/1982 | Komiya ........................ 606/47 |
| 5,261,418 A | * | 11/1993 | Ferek-Petric ................ 607/126 |
| 5,295,979 A | * | 3/1994 | DeLaurentis et al. ....... 604/265 |
| 5,395,312 A | * | 3/1995 | Desai ........................... 604/152 |
| 5,401,274 A | * | 3/1995 | Kusunoki ...................... 606/41 |
| 5,685,961 A | * | 11/1997 | Pourrezaei et al. ..... 204/192.14 |
| 5,755,766 A | * | 5/1998 | Chastian et al. ............. 607/122 |

FOREIGN PATENT DOCUMENTS

WO    WO 97/21849    6/1997    ........... C23C/18/30

OTHER PUBLICATIONS

Ghouse, Mohammad, "Platinum Deposition on Carbon Powder" of Metal Finishing of Jul. 1991, pp. 29–31.

* cited by examiner

Primary Examiner—Mark Bockelman
(74) Attorney, Agent, or Firm—Thomas J. Nikolai; Nikolai & Mersereau, P.A.

(57) ABSTRACT

A lead body for use with medical devices and method for lead body manufacture are provided. The lead body defines a lumen. The lumen has an electrically conductive material deposited on the lumen wall. The lead body's manufacture includes coating a lumen wall of a lead body with a conductive material to provide a conductor between the proximal and distal ends of the lead body. The manufacture further includes fitting sleeves electrically connected to electrical elements within the lumen to provide an electrical connection between the sleeve and the conductive material.

18 Claims, 4 Drawing Sheets

COIL-LESS LEAD SYSTEM

BACKGROUND OF THE INVENTION

1. Field of the Invention

The present invention relates generally to medical leads, and more particularly to implantable medical leads having conductive materials deposited within the lumen of the lead body.

2. Description of the Related Art

Implantable leads form an electrical connection between a pulse generator or other electronic device and a tissue or structure in the body. For example, leads transmit electric signals used to stimulate cardiac or nerve tissue in one direction and signals generated by sensors placed in proximity to particular organs or tissues in the opposite direction. Leads typically include one or more electric elements at the lead's distal end. The electric elements are designed to form an electrical connection with a tissue or organ. Most leads also include a lead connector pin at the lead's proximal end. Lead connector pins are adapted to electrically and mechanically connect leads to the pulse generators or other electronic medical devices. A conductor connects the electric element to the lead connector pin. Commonly, the conductor takes the form of a single or multifilar wire coil. Stranded cable conductors are also common. Regardless of the conductors form, an insulating layer of material typically surrounds the conductors. Together, the flexible conductor and the insulating layer form the lead body.

Lead bodies having coils or cables can suffer from a variety of disadvantages, including fractured coils/cables, coil corrosion, difficult assembly, limited flexibility, and size limitations among others. Flex fatigue is a particularly prevalent problem. Flex fatigue is the fatiguing of the conductors upon repeated flexing caused, for example, by the pumping of the heart. Flex fatigue can lead to the fracture of one or more conductors reducing or eliminating the lead's conductivity. This problem is exacerbated as coils are reduced in size. Closely related to fatigue is clavicle crush. Clavicle crush is the crushing of a lead implanted through the subclavian vein by the clavicle. The crushing can cause fracture of the conductors. Because of the need to access the heart through the subclavian vein, there is a need for a lead body more resistant to clavicle crush. Hence, a need exists for a lead that is more resistant to fracture due to flex fatigue, clavicle crush and other stresses that will be recognized by those skilled in the art.

The coils or cables also limit the minimum size for a lead body. Smaller diameter leads allow the placement of leads in more restricted spaces, such as cardiac veins or the epidural space, with a reduced affect on the patient relative to current lead sizes. Further, a smaller lead allows the use of smaller introducers that reduce the trauma associated with implantation. Similarly, a smaller removal sheath may also be used when explanting the reduced diameter lead. Hence, there exists a need to reduce the diameter of the lead bodies.

In addition, manufacturing leads is costly. Forming a secure electrical junction between the conductors and electric elements has proven difficult and time consuming. Laser welds are commonly used to connect the conductors to electric elements. Laser welding the coils to electric elements typically requires that the end of a coil be ground flat. Grinding the ends flat allows sufficient contact between the coil and the electrical element to weld the two together with a butt joint. Grinding increases the time, complexity and cost of manufacture. Further, welding may require the synchronized rotation of the conductor and electric element to weld at the various points around their circumference. The rotating also adds to the time, complexity and costs of manufacture. Alternatively, ring electrodes are connected to a conductor by etching away a region of insulator, applying a coating of electrically conductive adhesive, and then placing the ring electrode around the conductor. This method is also time consuming and expensive. Certain electrodes can also be crimped to the coiled or stranded conductor. Crimping, while a relatively simple process, places restrictions on the lead's design. Further, crimping is relatively time consuming and can add significantly to the products cost. Hence, there exists a need to improve the manufacturing techniques used to secure electric elements to conductors in leads to reduce the time, complexity and cost.

The present invention meets these needs and provides other advantages and improvements that will be evident to those skilled in the art upon review of the following figures and description.

SUMMARY OF THE INVENTION

The present invention provides a lead body having an electrically conductive coating deposited within its lumen. The lead body is more flexible than leads employing coils or cables and offers the advantage of increased fatigue life while decreasing susceptibility to damaging in vivo forces, such as clavicle crush. The present invention reduces the cost in time and materials for the manufacture of the lead body relative to lead bodies employing coils or cables as conductors. The costs are reduced by, inter alia, eliminating various processes and related equipment required to join the coil or cable to other electrical components such as distal electrodes or the terminal components. The lead body may be manufactured in smaller sizes and with greater flexibility than with current methods of manufacture. The conductive coating occupying only minimal space in the lead body compared to typical coils and cables facilitates this reduction in size. In addition, the lead body allows for a simplified electrical connection between the lead body and the associated electrodes and/or sensors further reducing the cost of manufacture. Further, the present invention provides a lead that may realize the above and other advantages while providing handling characteristic similar to that of current lead designs, if desired by the user.

A lead body in accordance with the present invention includes a body defining at least one lumen, the lumen having a lumen wall. A conductive material is deposited on the lumen wall to conduct an electric current. When there are a plurality of lumen, at least one lumen is coated with a conductive material. The conductive material may be substantially coextensive or coextensive with the wall of the lumen. The lumen may be any of a number of shapes such as round, oval, triangle, square, pentagon, hexagon, heptagon, octagon or other shapes. The lead body may further include a protective layer covering the conductive material. The protective layer may impart desired performance characteristics on the lead body, protect the conductive layer, or both impart performance characteristic and protect the conductive layer.

In another embodiment, the lead body may include an inner body received within a lumen of an outer body. The inner body defines a lumen, the lumen having a lumen wall. The inner body may have a conductive material deposited on its lumen wall to conduct an electric current. Additional inner bodies may be provided to fit within the body. Each of the plurality of bodies defining a lumen, each lumen having a wall, and a conductive material deposited on the walls of at least one of the bodies to conduct an electric current. The plurality of inner bodies are received within the lumen of the body. The additional inner bodies may have different outside diameters and lumen diameters. The outside and lumen diameters corresponding such that in descending order of size each smaller body is fitted within the lumen of the next larger body.

A lead in accordance with the present invention is manufactured by providing a lead body defining a lumen and depositing a conductive material on a wall of the lumen. The conductive material may be deposited by electroless deposition, plasma deposition, sputtering, chemical deposition or other methods that will be recognized by those skilled in the art.

Electric elements, such as electrodes and sensors, may be secured to a lead body by fitting a sleeve of the electrical element within the lead body's lumen to form an electrical contact between the electrical element and a conductive material. Further, electric elements may be secured to a lead body having an inner body and an outer body by fitting a sleeve of the electrical element between the inner body and the outer body to form an electrical contact between the electrical element and the conductive material. An adhesive that may itself be conductive may also be included to secure the sleeve within the lumen or between the bodies. Alternatively, the sleeve may be compressionally fit within the lumen or between the bodies. Again, an adhesive that may itself be conductive may also be included to secure the compressionally fit sleeve within the lumen or between the bodies.

DETAILED DESCRIPTION OF THE INVENTION

The present invention is applicable to a variety of implantable medical devices utilizing an electric current to stimulate selected body tissues or to transmit signals from a sensor or electrode contacting selected tissue to the medical device. The invention is described generally in the context of a lead body for a cardiac pacing lead for illustrative purposes only. The appended claims are not intended to be limited to any specific end use, example or embodiment described in this specification. It will be understood by those skilled in the art that the lead body of the present invention may be used in a wide variety of implantable leads including, but not limited to, neurostimulation leads, pacing leads, cardiac sensing leads, defibrillation leads, unipolar leads, multipolar leads, and leads with extendable positive helix fixation electrodes. Further, the numbers are repeated throughout the figures where the individual elements are substantially identical to one another.

Figure 1:
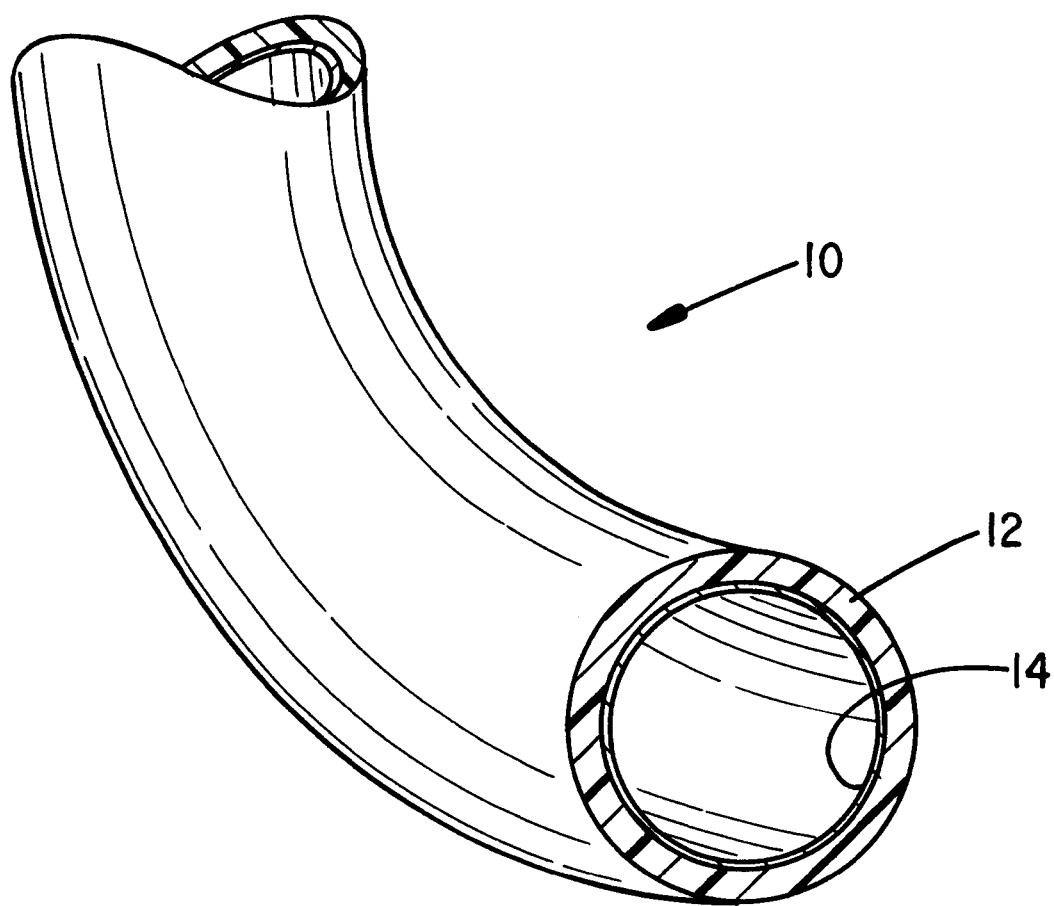
FIG. 1 illustrates a partial perspective view of a unipolar lead body in accordance with the present invention.
Figure 2A:
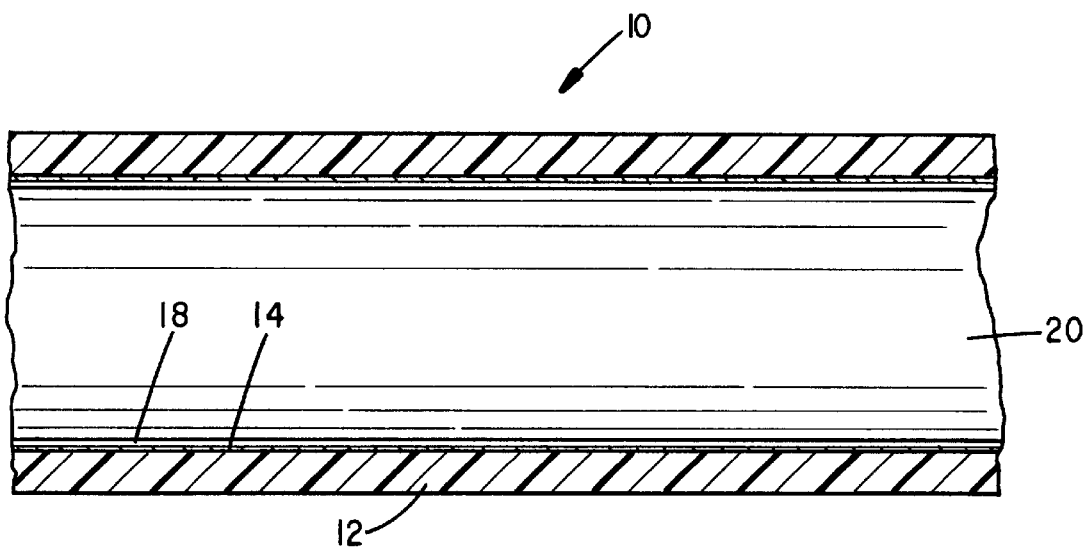
FIG. 2A illustrates a fragmentary longitudinal cross-section of a unipolar lead body in accordance with the present invention.
Figure 2B:
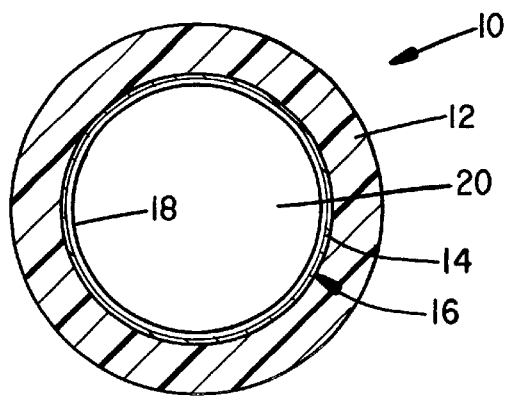
FIG. 2B illustrates an end view of a unipolar lead body as in FIG. 2A.

FIGS. 1, 2A and 2B illustrate a unipolar lead body 10 in accordance with the present invention. Lead body 10 comprises a body 12 defining a lumen 20. Lumen 20 has a conductive material 14 deposited on a lumen wall 16. In addition, conductive material 14 may be coated with a protective layer 18. Lead body 10 is generally configured to conduct an electric current between electrical elements, such as electrodes and sensors, connected to its proximal and distal ends. Further, lead body 10 is typically constructed to permit the implantation either permanent or temporary into a patient as required by the particular application for which the lead is used.

Body 12 is generally constructed to electrically insulate conductive material 14 from the patient. Body 12 typically has a round cross-section although the cross-section may be oval, triangular, square, rectangular, or other shape appropriate for the lead's particular application. Body 12 may be constructed from a flexible biocompatible material, such as silicones, polyurethanes, polyolefins, polyamides, polyesters, polyimides, fluoropolymers such as PTFE and ETFE, or other materials known to those skilled in the art. Body 12 can be extruded in the form of a body having a single or multiple lumen 20. Alternatively, body 12 may be molded, woven, knot braided or formed by other means known to those skilled in the art into the desired configuration.

Figure 3A:
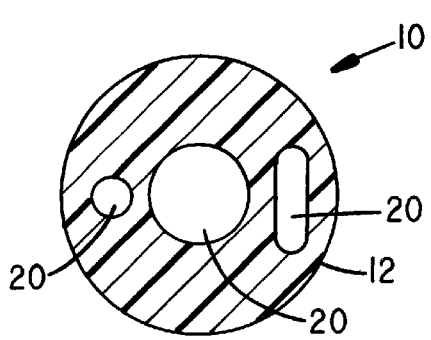
FIG. 3A illustrates transverse cross-section of an alternative embodiment for the lumen configuration.
Figure 3B:
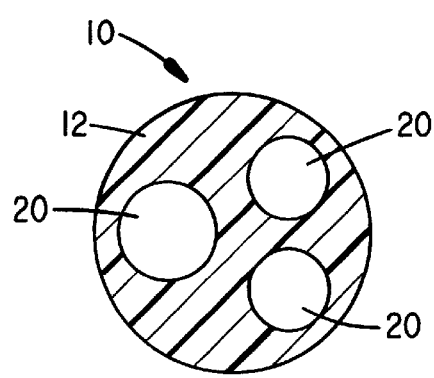
FIG. 3B illustrates transverse cross-section of another embodiment for the lumen configuration.

FIGS. 3A, 3B and 3C illustrate additional lumen configurations in accordance with the present invention. Lumen 20 typically extend from the proximal end to the distal end of the lead body. Lumen 20 may be round in cross-section although they may also be oval, triangular, square, rectangular, or other shape appropriate for the leads particular application as will be recognized by those skilled in the art. When lead body 10 includes a plurality of lumen 20, two or more lumen 20 may be coated with conductive material 14 to form a multipolar lead. In addition, lumen 20 not functioning as conductors may be configured for other applications such as drug delivery.

An electrically conductive material 14 is deposited on lumen wall 16 to transmit an electrical signal between the proximal and distal ends of the lead body. The conductive coating is typically deposited as a film. Conductive material 14 may be a metal such as platinum, palladium, iridium, nickel, silver, gold, copper, cobalt, titanium, other conductive metal; an alloy including any of these metals; or a conductive polymer such as polypyrrole and polyaniline. The possible materials also include metal oxides or nitrides such as iridium oxide and titanium nitride and various conductive forms of carbon.

Conductive material 14 may be deposited on lumen wall 16 using various methods. The conductive material may be deposited using electroless deposition, plasma deposition, sputtering, chemical deposition, or by other methods that will be recognized by those skilled in the art upon review of the present disclosure. U.S. Pat. No. 4,006,047, the disclosure of which is hereby incorporated by reference, discloses an exemplary method for electroless deposition of metal like gold, nickel or copper on polymeric substrates. Another method for depositing the conductive material is disclosed in the PCT application having International Publication Number WO 97/21849, published Jun. 19, 1997, the disclosure of which is hereby incorporated by reference. Electroless deposition allows conductive materials to be deposited on various substrates using a redox reaction to deposit the material without an electric current, as required when electroplating. Since electroless deposition uses a fixed concentration of the metal ion being deposited, the process can produce a substantially uniform metal film including along edges, on the lumen of tubing, inside cavities and over otherwise irregularly shaped substrates. Also, since the deposition of metal occurs only on catalyzed sites, different areas of the substrate can be masked to prevent the deposition of the coating, thereby giving the manufacturer precise control over the surfaces actually coated with the film. Suitable processes typically involve surface preparation, addition of the catalyst to the substrate surface, and deposition of the metal coating by reduction of a metal complex using a reducing agent.

As mentioned above, a protective layer 18 may be applied to the exposed surface of the conductive material. Typically, protective layer 18 is configured to prevent the abrading of the conductive material as the lumen receives a stylet during insertion or removal of the lead. Protective layer 18 may comprise a coating such as PTFE or other material deposited over the conductive material or may comprise an element such as a second body of suitable material place within the lumen of the lead body.

Protective layer 18 may be configured to impart desired performance characteristics on the lead body. For example, protective layer 18 may be constructed to approximate the physical characteristics of traditional leads to reduce the time necessary for a physician to become familiar with the lead body's handling characteristics. To accomplish this, a stiffer non-conductive body may be used. The stiffer non-conductive body is inserted into the lead body's lumen to protect the conductive layer and to provide the lead body with the desired handling performance. Alternatively, protective layer 18 may be formed by depositing a desired material on the exposed surface of the conductor in a manner similar to the deposition of the conductor.

Figure 4A:
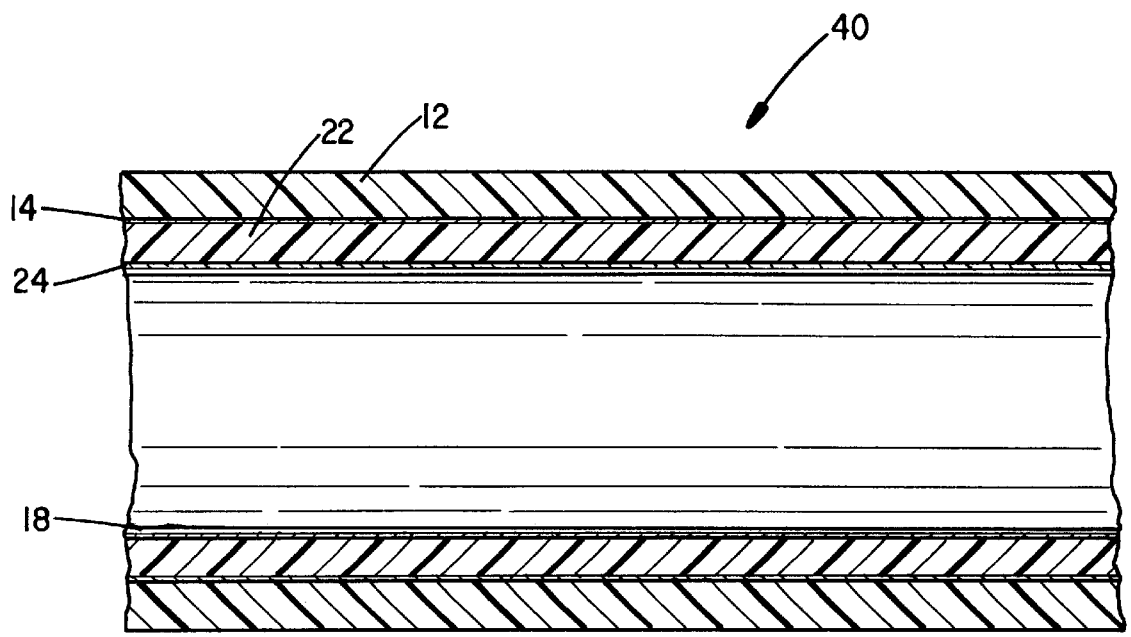
FIG. 4A illustrates a fragmentary longitudinal cross-section of a bipolar lead body in accordance with the present invention.
Figure 4B:
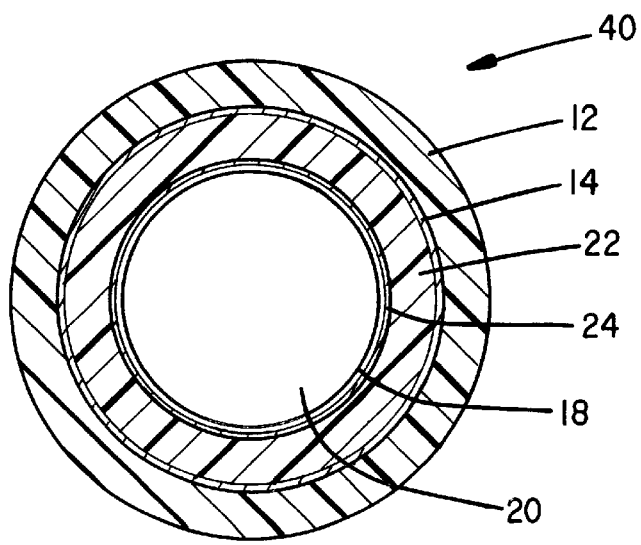
FIG. 4B illustrates a transverse cross-section of a bipolar lead body in accordance with the present invention.

FIGS. 4A and 4B illustrate an additional multipolar lead configuration in accordance with the present invention. Bipolar lead body 40 includes an outer body 12 and an inner body 22. Outer body 12 includes a conductive material 14 provided on the outer body's inner surface, as with body 12 of FIGS. 1, 2A and 2B. Inner body 22 is fit within outer body 22 and defines a lumen 20 that includes a conductive material 24 deposited on the lumen's wall. Inner body 22 is typically constructed from a flexible biocompatible material, such as silicones, polyurethanes, polyolefins, polyamides, polyesters, polyimides, fluoropolymers such as PTFE and ETFE, or other materials known to those skilled in the art. The material may be the same as or different from the material used for outer body 12. Inner body 22 protects the conductive material 14 and provides a substrate for the deposition of second conductive layer 24. In addition, a protective layer 18, as described above, may be provided to protect conductive material 24.

Figure 5:
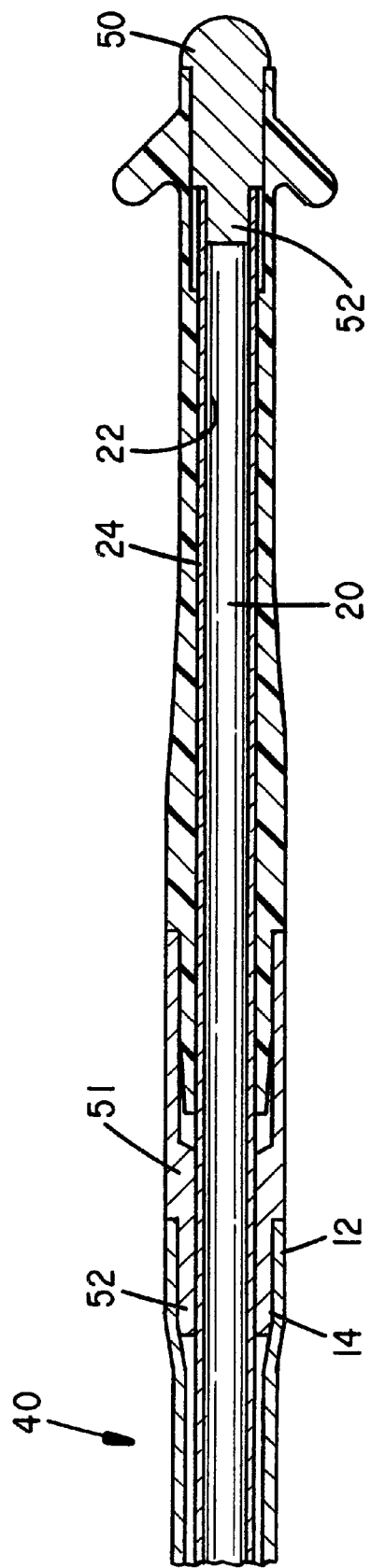
FIG. 5 illustrates a longitudinal cross-section of an embodiment of an electrode assembly at the distal end of a bipolar lead, as in FIGS. 3A and 3B.

FIG. 5 illustrates a connection between a bipolar lead body 40, substantially as shown in FIGS. 4A and 4B, and a first electrode 50 and a second electrode 51. First electrode 50 and second electrode 51 include conductive sleeves 52 configured to be received by lead body 40. Conductive sleeves 52 are electrically coupled to first electrode 50 and second electrode 51. Conductive sleeves 52 may be integral with the electrode or may be separate components attached to the electrodes. Generally, sleeve 52 of first electrode 50 may be fit into lumen 20 prior to coating the lumen with the conductive material. As shown, sleeve 52 of first electrode 50 is compressionally fit within lumen 20 of inner body 22 to electrically communicate with conductive material 24. In addition, an adhesive may be provided to further secure the compressionally fit conductive sleeve 51 within lumen 20. Alternatively, sleeve 52 of first electrode 50 may be place within lumen 20 and secured with a conductive adhesive. As shown, sleeve 52 of second electrode 51 is fit between conductive material 14 on outer body 12 and the outer surface of inner body 22. As shown, sleeve 52 of first electrode 51 is compressionally fit between outer body 12 and inner body 22 to electrically communicate with conductive material 14. In addition, an adhesive may be provided to further secure the compressionally fit conductive sleeve 52 between outer body 12 and inner body 22. Alternatively, sleeve 52 of first electrode 51 may be place between outer body 12 and inner body 22 and secured with a conductive adhesive.

what is claimed is:

1. A tissue stimulating lead body adapted for implantation in a patient, comprising:

a body defining a lumen, the lumen having a lumen wall, at least one electrode on a distal end of the body and at least one terminal on a proximal end of the body; and a conductive material deposited as a coating on the lumen wall to conduct an electric current between the at least one electrode and the at least one terminal.

2. The tissue stimulating lead body, as in claim 1, wherein the conductive material is substantially coextensive with the lumen wall.

3. A lead body, as in claim 1, further comprising:

an inner body received within the lumen of the body, the inner body defining a second lumen, the second lumen having a second lumen wall; and a conductive material deposited as a coating on the second lumen wall to conduct an electric current.

4. The tissue stimulating lead body, as in claim 1, wherein the lumen is in a shape selected from the group consisting of: round, oval, triangle, square, pentagon, hexagon, heptagon, and octagon.

5. The tissue stimulating lead body, as in claim 1, wherein the body further defines a plurality of lumens at least one lumen including the conductive material.

6. The tissue stimulating lead body, as in claim 1, further comprising a protective layer covering the conductive material.

7. The tissue stimulating lead body, as in claim 6, wherein the protective layer is a non-conductive coating deposited on the conductive material within the lumen.

8. The tissue stimulating lead body, as in claim 1, further comprising:

a plurality of bodies received within the lumen of the body, each of the plurality of bodies defining a lumen, each lumen having a lumen wall; and a conductive material deposited as a coating on the lumen walls of the plurality of bodies to conduct an electric current.

9. The tissue stimulating lead body, as in claim 8, wherein each of the plurality of bodies has a different outside diameter and a different inside diameter such that in descending order of size, each smaller body is fitted within the lumen of the next larger body.

10. A method for manufacturing a tissue stimulating lead body, comprising:

providing an insulating body defining a lumen;

affixing an electrode to a distal end of the body;

affixing a terminal to a proximal end of the body; and depositing a conductive material as a coating on a wall of the lumen for connecting the terminal to the electrode.

11. A method, as in claim 10, wherein the method for depositing the conductive material on the wall of the lumen is selected from the group consisting of electroless deposition, plasma deposition, sputtering, and chemical deposition.

12. A method, as in claim 10, wherein the conductive material is selected from the group consisting of platinum, palladium, iridium, nickel, silver, gold, copper titanium and cobalt.

13. A method, as in claim 10, wherein the conductive material is an alloy including a metal selected from the group consisting of platinum, iridium, nickel, silver, gold, copper, titanium and cobalt.

14. A method of manufacturing a tissue stimulating lead body comprising:

providing an insulating body defining a lumen;

affixing an electrode to a distal end of the body;

affixing a terminal to the proximal end of the body;

and deposing a coating of a conductive material that comprises a conductive polymer selected from the group consisting of polypyrrole and polyaniline.

15. A method, as in claim 10, wherein the conductive material is an oxide of a metal selected from the group consisting of platinum, iridium, nickel, silver, gold, copper, titanium and cobalt.

16. A method, as in claim 10, wherein the conductive material is a nitride of a metal selected from the group consisting of platinum, iridium, nickel, silver, gold, copper, titanium and cobalt.

17. A method, as in claim 10, wherein the conductive material is a conductive form of carbon.

18. A method, as in claim 10, wherein the lead body is composed of a polymer selected from the group consisting of silicones, polyurethanes, polyolefins, polyamides, polyesters, polyimides, and fluoropolymers.

* * * * *